(12) United States Patent
Shultz et al.

(10) Patent No.: US 8,952,138 B2
(45) Date of Patent: *Feb. 10, 2015

(54) REFOLDING PROTEINS USING A CHEMICALLY CONTROLLED REDOX STATE

(75) Inventors: Joseph Edward Shultz, Santa Rosa Valley, CA (US); Roger Hart, Loveland, CO (US); Ronald Nixon Keener, III, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 403 days.

This patent is subject to a terminal disclaimer.

(21) Appl. No.: 12/820,087

(22) Filed: Jun. 21, 2010

(65) Prior Publication Data

US 2010/0324269 A1 Dec. 23, 2010

Related U.S. Application Data

(60) Provisional application No. 61/219,257, filed on Jun. 22, 2009.

(51) Int. Cl.
C07K 1/22 (2006.01)
C07K 1/113 (2006.01)

(52) U.S. Cl.
CPC .................................. C07K 1/1133 (2013.01)
USPC ........................................................ 530/413

(58) Field of Classification Search
None
See application file for complete search history.

(56) References Cited

U.S. PATENT DOCUMENTS

| | | | |
|---|---|---|---|
| 6,660,843 B1 | 12/2003 | Feige et al. | |
| 6,808,902 B1 | 10/2004 | Treuheit et al. | |
| 7,138,370 B2 | 11/2006 | Oliner et al. | |
| 7,511,012 B2 | 3/2009 | Han et al. | |
| 7,723,490 B2 | 5/2010 | Treuheit et al. | |
| 2008/0214795 A1 | 9/2008 | Ramanan et al. | |
| 2010/0267936 A1 | 10/2010 | Treuheit et al. | |

FOREIGN PATENT DOCUMENTS

| | | | |
|---|---|---|---|
| EP | 1845103 A1 | 10/2007 | |
| WO | 92/04382 A1 | 3/1992 | |
| WO | 99/42486 A1 | 8/1999 | |

OTHER PUBLICATIONS

Cowley, D,J, & Mackin, R.B., "Expression, purification and characterization of recombinant human proinsulin," FEBS Lett 402:125-130 (1997).
De Bernardez Clark, Eliana, et al. "Oxidative Renaturation of Hen Egg-White Lysozyme, Folding vs aggregation." Biotechnol, Prog. 14: 47-57 (1998).
Rudolph & Lilie, "In vitro folding of inclusion body proteins," FASEB J. 10:49-56 (1996).
Creighton, T.E., "Renaturation of the reduced bovine pancreatic trypsin inhibitor,"J. Mol. Biol. 87:563-577 (1974).
Stöckel, Johannes, et al., "Pathway of detergent-mediated and peptide ligand-mediated refolding of heterodimeric class II major histocompatibility complex (MHC) molecules," Eur J Biochem 248:684-691 (1997).
St John et al., "High pressure refolding of recombinant human growth hormone from insoluble aggregates. Structural transformations, kinetic barriers, and energetics," J. Biol. Chem. 276(50):46856-63 (2001).
Lilie, Schwarz & Rudolph, "Advances in refolding of proteins roduced in *E. coli*," Current Opinion in Biotechnology 9 (5):497-501 (1998).
Tran-Moseman, Schauer & Clark, "Renaturation of*Escherichla coli*—Derived Recombinant Human Macrophage Colony-Stimulating Factor," Protein Expression & Purification 16(1):181-189 (1999).
Darby, N.J., et al., "Refolding of Bovine Pancreatic Trypsin InhibitorviaNon-native Disulphide Intermediate," J Molecular Biol. 249(2):463-477 (1995).
Wang, Xi-De, "Perturbation of the antigen-binding site and staphylococcal protein A-binding site of IgG before significant changes in global conformation during denaturation: an equilibrium study,"Biochem. Prog. 14; 47-54 (1998).
Singh el al., "Solubilization and Refolding of Bacterial Inclusion Body Proteins," J. Bioscience and Bioengineering, vol. 99(4), pp. 303-310 (2005).
DeBernadez Clark, Eliana, "Refolding of recombinant proteins," Current Opinion in Biotechnology, vol. 9 p. 157-163 (1998).
DuBernardez Clark, Eliana, "Protein Refoldng for industrial processes," Current Opinion in Biotechnology, vol. 12, pp. 202-207 (2001).
Javaherian, K. et al., "Laminin Modulates Morphogenic Properties of the Collagen XVIII Endostatin Domain," *J. Biol. Chem.* 277(47):45211-45218, Nov. 22, 2002.

*Primary Examiner* — Yunsoo Kim
(74) *Attorney, Agent, or Firm* — David B. Ran

(57) ABSTRACT

A method of refolding proteins expressed in non-mammalian cells present in concentrations of 2.0 g/L or higher is disclosed. The method comprises identifying the thiol pair ratio and the redox buffer strength to achieve conditions under which efficient folding at concentrations of 2.0 g/L or higher is achieved and can be employed over a range of volumes, including commercial scale.

24 Claims, 8 Drawing Sheets

REFOLDING PROTEINS USING A CHEMICALLY CONTROLLED REDOX STATE

This application claims the benefit of U.S. Provisional Application No. 61/219,257 filed Jun. 22, 2009, which is incorporated by reference herein.

FIELD OF THE INVENTION

The present invention generally relates to refolding proteins at high concentrations, and more particularly to refolding proteins in volumes at concentrations of 2.0 g/L and above.

BACKGROUND OF THE INVENTION

Recombinant proteins can be expressed in a variety of expression systems, including non-mammalian cells, such as bacteria and yeast. A difficulty associated with the expression of recombinant proteins in prokaryotic cells, such as bacteria, is the precipitation of the expressed proteins in limited-solubility intracellular precipitates typically referred to as inclusion bodies. Inclusion bodies are formed as a result of the inability of a bacterial host cell to fold recombinant proteins properly at high levels of expression and as a consequence the proteins become insoluble. This is particularly true of prokaryotic expression of large, complex or protein sequences of eukaryotic origin. Formation of incorrectly folded recombinant proteins has, to an extent, limited the commercial utility of bacterial fermentation to produce recombinant large, complex proteins, at high levels of efficiency.

Since the advent of the recombinant expression of proteins at commercially viable levels in non-mammalian expression systems such as bacteria, various methods have been developed for obtaining correctly folded proteins from bacterial inclusion bodies. These methods generally follow the procedure of expressing the protein, which typically precipitates in inclusion bodies, lysing the cells, collecting the inclusion bodies and then solubilizing the inclusion bodies in a solubilization buffer comprising a denaturant or surfactant and optionally a reductant, which unfolds the proteins and disassembles the inclusion bodies into individual protein chains with little to no structure. Subsequently, the protein chains are diluted into or washed with a refolding buffer that supports renaturation to a biologically active form. When cysteine residues are present in the primary amino acid sequence of the protein, it is often necessary to accomplish the refolding in an environment which allows correct formation of disulfide bonds (e.g., a redox system).

Typical refold concentrations for complex molecules, such as molecules comprising two or more disulfides, are less than 2.0 g/L and more typically 0.01-0.5 g/L (Rudolph & Lilie, (1996) *FASEB J.* 10:49-56). Thus, refolding large masses of a complex protein, such as an antibody, peptibody or other Fc fusion protein, at industrial production scales poses significant limitations due to the large volumes required to refold proteins, at these typical product concentration, and is a common problem facing the industry. One factor that limits the refold concentration of these types of proteins is the formation of incorrectly paired disulfide bonds, which may in turn increase the propensity for those forms of the protein to aggregate. Due to the large volumes of material and large pool sizes involved when working with industrial scale protein production, significant time, and resources can be saved by eliminating or simplifying one or more steps in the process.

While protein refolding has previously been demonstrated at higher concentrations, the proteins that were refolded were either significantly smaller in molecular weight, less complex molecules containing only one or two disulfide bonds (see, e.g., Creighton, (1974) *J. Mol. Biol.* 87:563-577). Additionally, the refolding processes for such proteins employed detergent-based refolding chemistries (see, e.g., Stockel et al., (1997) *Eur J Biochem* 248:684-691) or utilized high pressure folding strategies (St John et al., (2001) *J. Biol. Chem.* 276(50):46856-63). More complex molecules, such as antibodies, peptibodies and other large proteins, are generally not amenable to detergent refold conditions and are typically refolded in chaotropic refold solutions. These more complex molecules often have greater than two disulfide bonds, often between 8 and 24 disulfide bonds, and can be multi-chain proteins that form homo- or hetero-dimers.

Until the present disclosure, these types of complex molecules could not be refolded at high concentrations, i.e., concentrations of 2.0 g/L and higher, with any meaningful degree of efficiency on a small scale, and notably not on an industrial scale. The disclosed methods, in contrast, can be performed at high concentrations on a small or large (e.g, industrial) scale to provide properly refolded complex proteins. The ability to refold proteins at high concentrations and at large scales can translate into not only enhanced efficiency of the refold operation itself, but also represents time and cost savings by eliminating the need for additional equipment and personnel. Accordingly, a method of refolding proteins present in high concentrations could translate into higher efficiencies and cost savings to a protein production process.

BRIEF DESCRIPTION OF THE DRAWINGS

FIG. 1 is a series of plots depicting depicting the effect of thiol-pair ratio and redox buffer strength on product-species distribution.

SUMMARY OF THE INVENTION

Figure 1A:
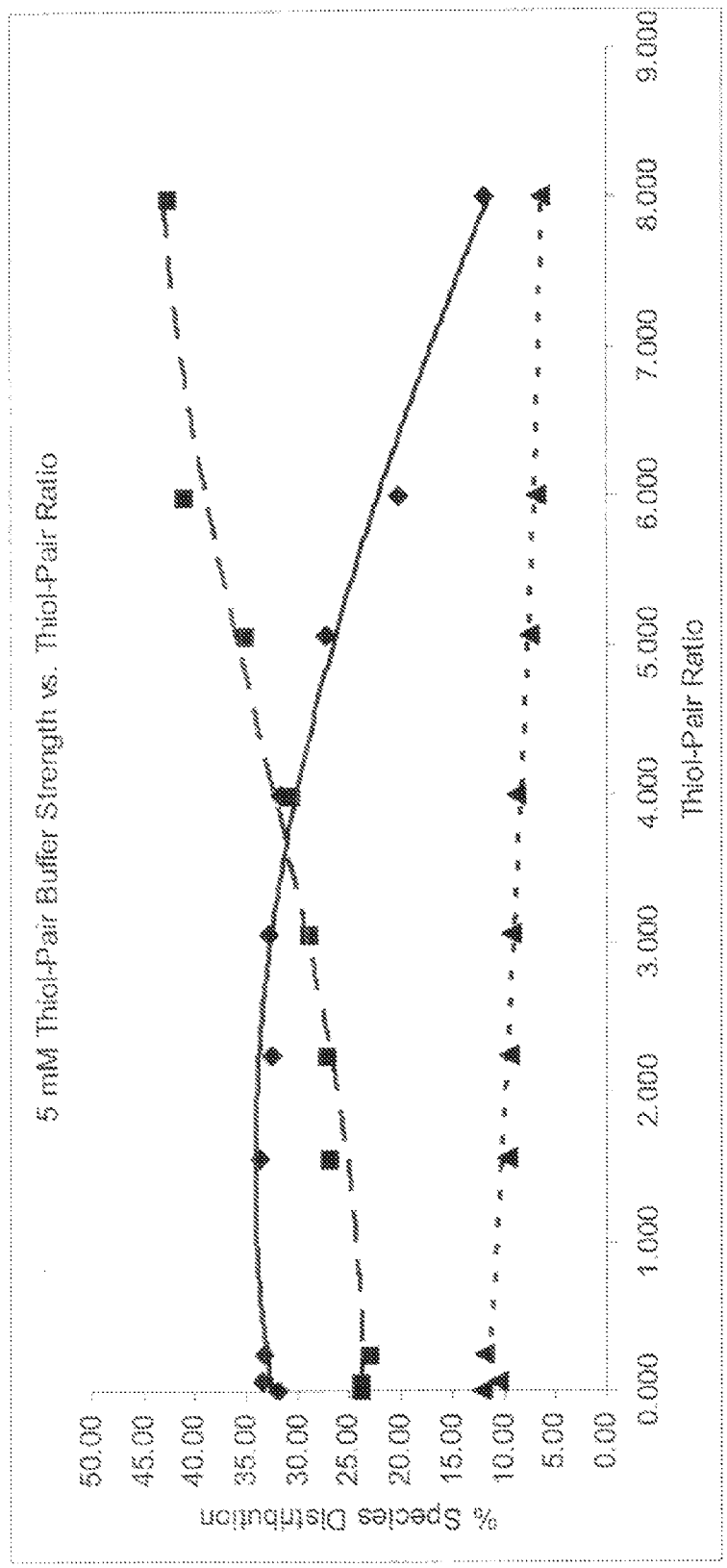
FIG. 1*a* depicts the effect of a 5 mM buffer strength.
Figure 1B:
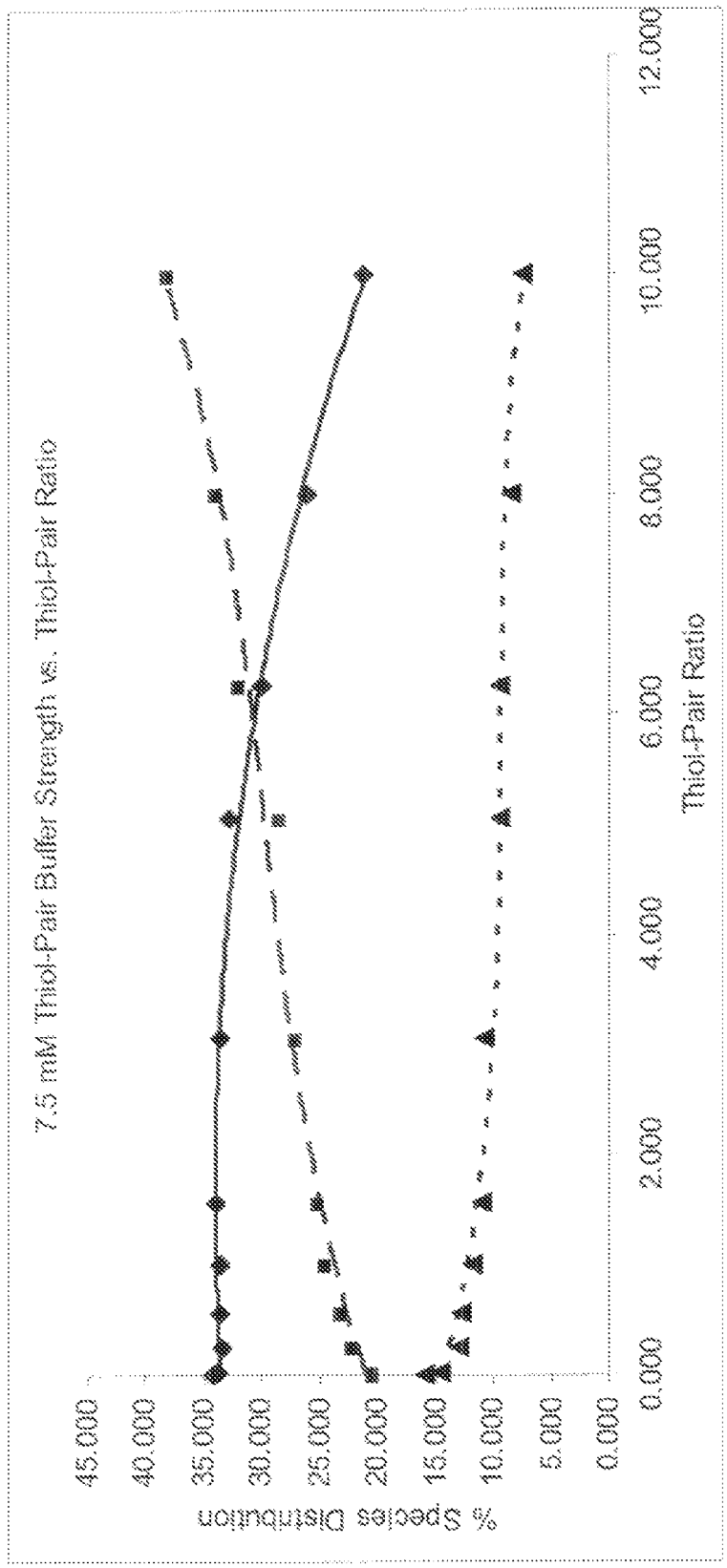
FIG. 1*b* depicts the effect of a 7.5 mM buffer strength.
Figure 1C:
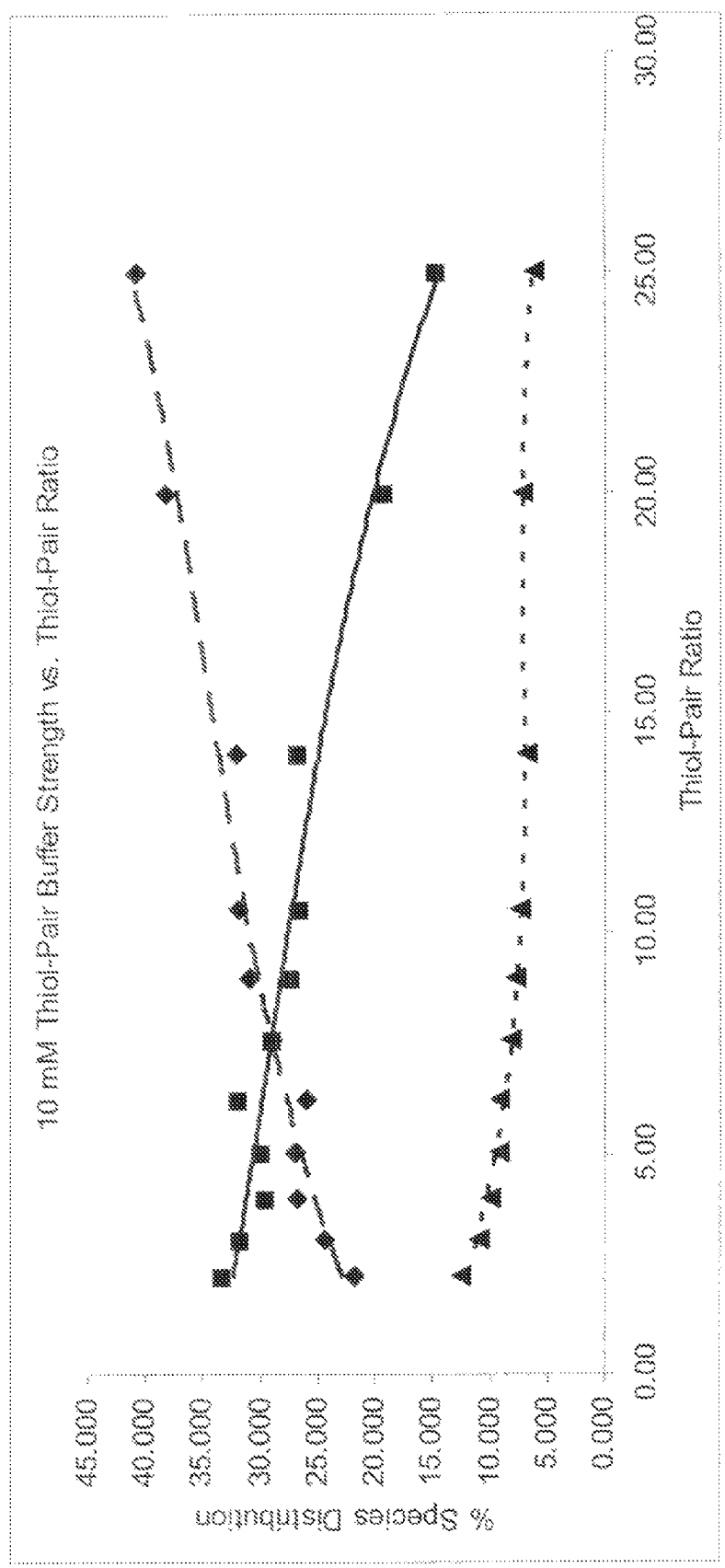
FIG. 1*c* depicts the effect of a 10 mM buffer strength.
Figure 1D:
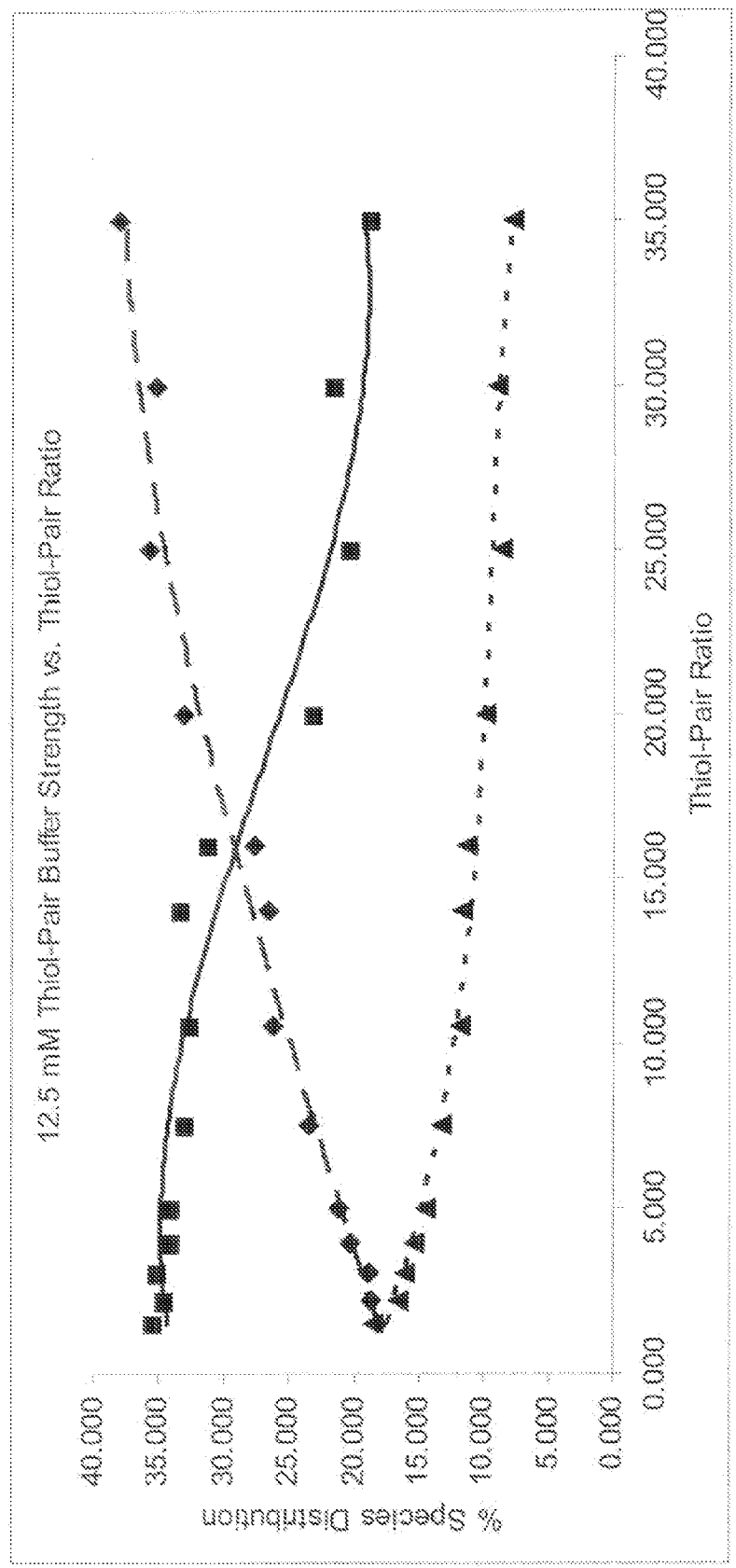
FIG. 1*d* depicts the effect of a 12.5 mM buffer strength.
Figure 1E:
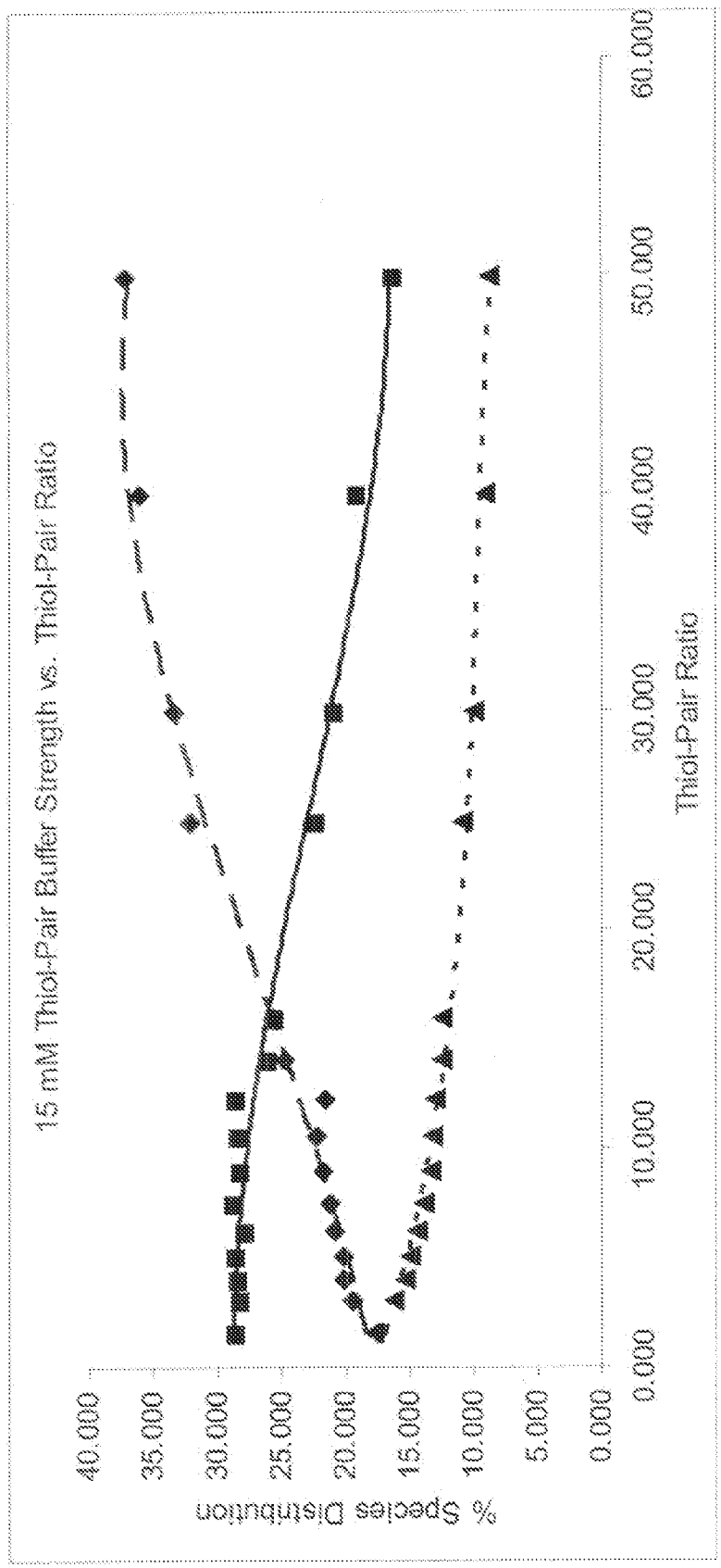
FIG. 1*e* depicts the effect of a 15 mM buffer strength and FIG. 1*f* depicts the effect of a 20 mM buffer strength.
Figure 1F:
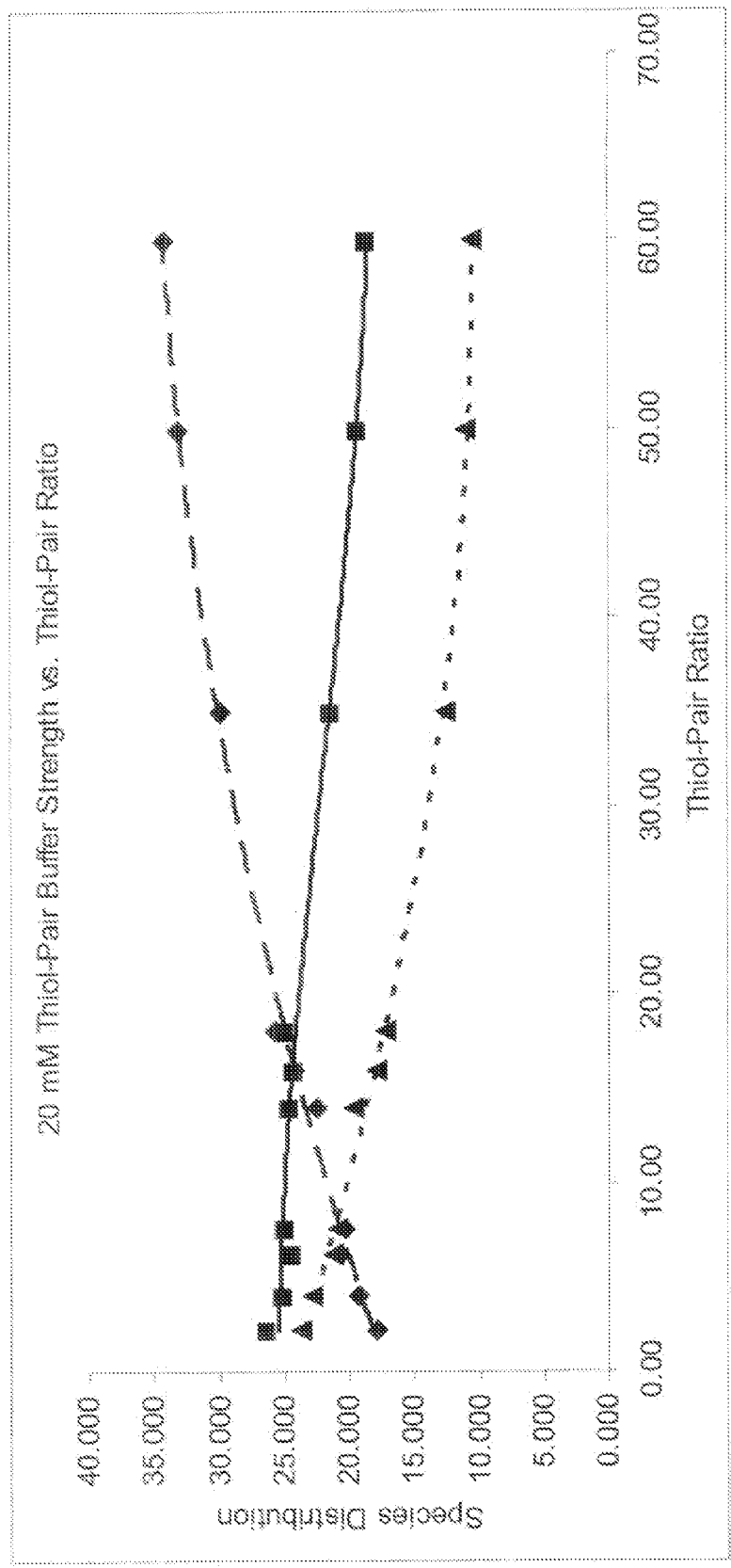

A method of refolding a protein expressed in a non-mammalian expression system and present in a volume at a concentration of 2.0 g/L or greater comprising: (a) contacting the protein with a refold buffer comprising a redox component comprising a final thiol-pair ratio having a range of 0.001 to 100 and a redox buffer strength of 2 mM or greater and one or more of: (i) a denaturant; (ii) an aggregation suppressor; and (iii) a protein stabilizer; to form a refold mixture; (b) incubating the refold mixture; and (c) isolating the protein from the refold mixture.

In various embodiments the redox component has a final thiol-pair ratio greater than or equal to 0.001 but less than or equal to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50 and a Thiol-pair buffer strength equal to or greater than 2 mM, for example greater than or equal to 2.25 mM, 2.5 mM, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength can be between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM, to form a mixture.

In one embodiment of a refold buffer, the refold buffer comprises urea, arginine-HCl, cysteine and cystamine in Tris buffer. In a further embodiment the components are present in the refold buffer in proportions described in Example 3.

In another embodiment of a refold buffer, the refold buffer comprises urea, arginine HCl, glycerol, cysteine, and cystamine in Tris buffer. In a further embodiment the components are present in the refold buffer in proportions described in Example 4.

In some embodiments, the protein is initially present in a volume in a non-native limited solubility form, such as an inclusion body. Alternatively, the protein is present in the volume in a soluble form. The protein can be a recombinant protein or it can be an endogenous protein. The protein can be a complex protein such as an antibody or a multimeric protein. In another embodiment, the protein is an Fc-protein conjugate, such as a protein fused or linked to a Fc domain.

The non-mammalian expression system can be a bacterial expression system or a yeast expression system.

The denaturant in the refold buffer can be selected from the group consisting of urea, guanidinium salts, dimethyl urea, methylurea and ethylurea. The protein stabilizer in the refold buffer can be selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes. The aggregation suppressor can be selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes. The thiol-pairs can comprise at least one component selected from the group consisting of glutathione-reduced, glutathione-oxidized, cysteine, cystine, cysteamine, cystamine and beta-mercaptoethanol.

In various embodiments, the purification can comprise contacting the mixture with an affinity separation matrix, such as a Protein A or Protein G resin. Alternatively, the affinity resin can be a mixed mode separation matrix or an ion exchange separation matrix. In various aspects, the incubation can be performed under aerobic conditions or under non-aerobic conditions.

DETAILED DESCRIPTION OF THE INVENTION

The relevant literature suggests that when optimizing various protein refolding operations, the refold buffer thiol-pair ratio has been purposefully varied and as a result the thiol buffer strength was unknowingly varied across a wide range of strengths (see, e.g., Lille, Schwarz & Rudolph, (1998) Current Opinion in Biotechnology 9(5):497-501, and Tran-Moseman, Schauer & Clark (1999) Protein Expression & Purification 16(1):181-189). In one study, a relationship between the thiol pair ratio and the buffer strength was investigated for lysozyme, a simple, single-chain protein that forms a molten globule. (De Bernardez et al., (1998) Biotechnol. Prog. 14:47-54). The De Bernardez work described thiol concentration in terms of a model that considered only the kinetics of a one-way reaction model. However, most complex proteins are governed by reversible thermodynamic equilibria that are not as easily described (see, e.g., Darby et al., (1995) J. Mol. Biol. 249:463-477). More complex behavior is expected in the case of large multi-chain proteins containing many disulfide bonds, such as antibodies, peptibodies and other Fc fusion proteins. Until the present disclosure, specific relationships had not been provided for thiol buffer strength, thiol-pair ratio chemistry, and protein concentration with respect to complex proteins that related to the efficiency of protein production. Consequently, the ability to refold proteins in a highly concentrated volume has largely been an inefficient or unachievable goal, leading to bottlenecks in protein production, particularly on the industrial scale.

Prior to the present disclosure a specific controlled investigation of the independent effects of thiol-pair ratio and thiol-pair buffer strength had not been disclosed for complex proteins. As described herein, by controlling the thiol-pair buffer strength, in conjunction with thiol-pair ratio and protein concentration, the efficiency of protein folding operations can be optimized and enhanced and the refolding of proteins at high concentrations, for example 2 g/L or greater, can be achieved.

Thus, in one aspect, the present disclosure relates to the identification and control of redox thiol-pair ratio chemistries that facilitate protein refolding at high protein concentrations, such as concentrations higher than 2.0 g/L. The method can be applied to any type of protein, including simple proteins and complex proteins (e.g., proteins comprising 2-23 disulfide bonds or greater than 250 amino acid residues, or having a MW of greater than 20,000 daltons), including proteins comprising a Fc domain, such as antibodies, peptibodies and other Fc fusion proteins, and can be performed on a laboratory scale (typically milliliter or liter scale), a pilot plant scale (typically hundreds of liters) or an industrial scale (typically thousands of liters). Examples of complex molecules known as peptibodies, and other Fc fusions, are described in U.S. Pat. Nos. 6,660,843, 7,138,370 and 7,511,012.

As described herein, the relationship between thiol buffer strength and redox thiol-pair ratio has been investigated and optimized in order to provide a reproducible method of refolding proteins at concentrations of 2.0 g/L and higher on a variety of scales. A mathematical formula was deduced to allow the precise calculation of the ratios and strengths of individual redox couple components to achieve matrices of buffer thiol-pair ratio and buffer thiol strength. Once this relationship was established, it was possible to systematically demonstrate that thiol buffer strength and the thiol-pair ratio interact to define the distribution of resulting product-related species in a refolding reaction.

The buffer thiol-pair ratio is, however, only one component in determining the total system thiol-pair ratio in the total reaction. Since the cysteine residues in the unfolded protein are reactants as well, the buffer thiol strength needs to vary in proportion with increases in protein concentration to achieve the optimal system thiol-pair ratio. Thus, in addition to demonstrating that buffer thiol strength interacts with the thiol-pair ratio, it has also been shown that the buffer thiol strength relates to the protein concentration in the total reaction as well. Optimization of the buffer thiol strength and the system thiol pair ratio can be tailored to a particular protein, such as a complex protein, to minimize cysteine mispairing yet still facilitate a refold at a high concentration.

I. Definitions

As used herein, the terms "a" and "an" mean one or more unless specifically indicated otherwise.

As used herein, the term "non-mammalian expression system" means a system for expressing proteins in cells derived from an organism other than a mammal, including but not limited to, prokaryotes, including bacteria such as E. coli, and yeast. Often a non-mammalian expression system is employed to express a recombinant protein of interest, while in other instances a protein of interest is an endogenous protein that is expressed by a non-mammalian cell. For purposes of the present disclosure, regardless of whether a protein of interest is endogenous or recombinant, if the protein is expressed in a non-mammalian cell then that cell is a "non-mammalian expression system." Similarly, a "non-mammalian cell" is a cell derived from an organism other than a mammal, examples of which include bacteria or yeast.

As used herein, the term "denaturant" means any compound having the ability to remove some or all of a protein's secondary and tertiary structure when placed in contact with the protein. The term denaturant refers to particular chemical compounds that affect denaturation, as well as solutions comprising a particular compound that affect denaturation. Examples of denaturants that can be employed in the disclosed method include, but are not limited to, urea, guanidinium salts, dimethyl urea, methylurea, ethylurea and combinations thereof.

As used herein, the term "aggregation suppressor" means any compound having the ability to disrupt and decrease or eliminate interactions between two or more proteins. Examples of aggregation suppressors can include, but are not limited to, amino acids such as arginine, proline, and glycine; polyols and sugars such as glycerol, sorbitol, sucrose, and trehalose; surfactants such as, polysorbate-20, CHAPS, Triton X-100, and dodecyl maltoside; and combinations thereof.

As used herein, the term "protein stabilizer" means any compound having the ability to change a protein's reaction equilibrium state, such that the native state of the protein is improved or favored. Examples of protein stabilizers can include, but are not limited to, sugars and polyhedric alcohols such as glycerol or sorbitol; polymers such as polyethylene glycol (PEG) and α-cyclodextrin; amino acids salts such as arginine, proline, and glycine; osmolytes and certain Hoffmeister salts such as Tris, sodium sulfate and potassium sulfate; and combinations thereof.

As used herein, the terms "Fc" and "Fc region" are used interchangeably and mean a fragment of an antibody that comprises human or non-human (e.g., murine) $C_{H2}$ and $C_{H3}$ immunoglobulin domains, or which comprises two contiguous regions which are at least 90% identical to human or non-human $C_{H2}$ and $C_{H3}$ immunoglobulin domains. An Fc can but need not have the ability to interact with an Fc receptor. See, e.g., Hasemann & Capra, "Immunoglobulins: Structure and Function," in William E. Paul, ed., *Fundamental Immunology*, Second Edition, 209, 210-218 (1989), which is incorporated by reference herein in its entirety.

As used herein, the terms "protein" and "polypeptide" are used interchangeably and mean any chain of at least five naturally or non-naturally occurring amino acids linked by peptide bonds.

As used herein, the terms "isolated" and "purify" are used interchangeably and mean to reduce by 1%, 2%, 3%, 4%, 5%, 10%, 15%, 20%, 25%, 30%, 35%, 40%, 45%, 50%, 55%, 60%, 65%, 70%, 75%, 80%, 85%, 90% or 95%, or more, the amount of heterogenous elements, for example biological macromolecules such as proteins or DNA, that may be present in a sample comprising a protein of interest. The presence of heterogenous proteins can be assayed by any appropriate method including High-performance Liquid Chromatography (HPLC), gel electrophoresis and staining and/or ELISA assay. The presence of DNA and other nucleic acids can be assayed by any appropriate method including gel electrophoresis and staining and/or assays employing polymerase chain reaction.

As used herein, the term "complex molecule" means any protein that is (a) larger than 20,000 MW, or comprises greater than 250 amino acid residues, and (b) comprises two or more disulfide bonds in its native form. A complex molecule can, but need not, form multimers. Examples of complex molecules include but are not limited to, antibodies, peptibodies and other chimeric molecules comprising an Fc domain and other large proteins. Examples of complex molecules known as peptibodies, and other Fc fusions, are described in U.S. Pat. Nos. 6,660,843, 7,138,370 and 7,511,012.

As used herein, the term "peptibody" refers to a polypeptide comprising one or more bioactive peptides joined together, optionally via linkers, with an Fc domain. See U.S. Pat. Nos. 6,660,843, 7,138,370 and 7,511,012 for examples of peptibodies.

As used herein, the term "refolding" means a process of reintroducing secondary and tertiary structure to a protein that has had some or all of its native secondary or tertiary structure removed, either in vitro or in vivo, e.g., as a result of expression conditions or intentional denaturation and/or reduction. Thus, a refolded protein is a protein that has had some or all of its native secondary or tertiary structure reintroduced.

As used herein, the term "buffer thiol-pair ratio" is defined by the relationship of the reduced and oxidized redox species used in the refold buffer as defined in Equation 1:

$$\text{Definition of Buffer Thiol-Pair Ratio } (TPR) \qquad \text{Equation 1}$$

$$\text{Buffer } TPR = \frac{[\text{reductant}]^2}{[\text{oxidant}]} = \frac{[\text{cysteine}]^2}{[\text{cystamine}]}.$$

As used herein, the terms "Buffer Thiol Strength", "Thiol-Pair Buffer Strength", and "Thiol-pair Strength" are used interchangeably and are defined in Equation 2, namely as the total mono-equivalent thiol concentration, wherein the total concentration is the sum of the reduced species and twice the concentration of the oxidized species.

Definition of Buffer Thiol-Pair Buffer Strength/Thiol Buffer Strength (BS) Thiol-Pair Buffer Strength=2[oxidant]+[reductant]=2[cystamine]+[cysteine]        Equation 2.

The relationship between the thiol-pair ratio and thiol-pair buffer strength is described in equations 3 and 4.

Calculation of the Reduced Redox Species      Equation 3 with Regard to a Defined Redox Buffer

Strength (BS) and buffer Redox Potential $$\text{Concentration of Reduced Redox Component} = \frac{\left(\sqrt{bufferTPR^2 + 8*bufferTPR*BS}\right) - bufferTPR}{4}.$$

Calculation of the Oxidized Redox Species      Equation 4 with Regard to a Defined Redox Buffer

Strength (BS) and Buffer Redox Potential $$\text{Concentration of Oxidized Redox Component} = \frac{(\text{Concentration of Reduced Redox Component})^2}{TPR}.$$

As used herein, the term "redox component" means any thiol-reactive chemical or solution comprising such a chemical that facilitates a reversible thiol exchange with another thiol or the cysteine residues of a protein. Examples of such compounds include, but are not limited to, glutathione-reduced, glutathione-oxidized, cysteine, cystine, cysteamine, cystamine, beta-mercaptoethanol and combinations thereof.

As used herein, the term "solubilization" means a process in which salts, ions, denaturants, detergents, reductants and/or other organic molecules are added to a solution comprising a protein of interest, thereby removing some or all of a protein's secondary and/or tertiary structure and dissolving the protein into the solvent. This process can include the use of elevated temperatures, typically 10-50° C., but more typically 15-25° C., and/or alkaline pH, such as pH 7-12. Solubilization can also be accomplished by the addition of acids, such as 70% formic acid (see, e.g., Cowley & Mackin (1997) *FEBS Lett* 402:124-130).

A "solubilized protein" is a protein in which some or all of the protein's secondary and/or tertiary structure has been removed.

A "solublization pool" is a volume of solution comprising a solubilized protein of interest as well as the salts, ions, denaturants, detergents, reductants and/or other organic molecules selected to solubilize the protein.

As used herein, the term "non-aerobic condition" means any reaction or incubation condition that is performed without the intentional aeration of the mixture by mechanical or chemical means. Under non-aerobic conditions oxygen can be present, as long as it is naturally present and was not introduced into the system with the intention of adding oxygen to the system. Non-aerobic conditions can be achieved by, for example, limiting oxygen transfer to a reaction solution by limiting headspace pressure, the absence of, or limited exposure to, air or oxygen contained in the holding vessel, air or oxygen overlay, the lack of special accommodations to account for mass transfer during process scaling, or the absence of gas sparging or mixing to encourage the presence of oxygen in the reaction system. Non-aerobic conditions can also be achieved by intentionally limiting or removing oxygen from the system via chemical treatment, headspace overlays or pressurization with inert gases or vacuums, or by sparging with gases such as argon or nitrogen, results in the reduction of oxygen concentration in the reaction mixture.

As used herein, the terms "non-native" and "non-native form" are used interchangeably and when used in the context of a protein of interest, such as a protein comprising a Fc domain, mean that the protein lacks at least one formed structure attribute found in a form of the protein that is biologically active in an appropriate in vivo or in vitro assay designed to assess the protein's biological activity. Examples of structural features that can be lacking in a non-native form of a protein can include, but are not limited to, a disulfide bond, quaternary structure, disrupted secondary or tertiary structure or a state that makes the protein biologically inactive in an appropriate assay. A protein in a non-native form can but need not form aggregates.

As used herein, the term "non-native limited solubility form" when used in the context of a protein of interest, such as a protein comprising a Fc domain, means any form or state in which the protein lacks at least one formed structural feature found in a form of the protein that (a) is biologically active in an appropriate in vivo or in vitro assay designed to assess the protein's biological activity and/or (b) forms aggregates that require treatment, such as chemical treatment, to become soluble. The term specifically includes proteins existing in inclusion bodies, such as those sometimes found when a recombinant protein is expressed in a non-mammalian expression system.

II. Theory

Refolding microbial-derived molecules present in a pool at concentrations of 2.0 g/L or higher is advantageous for a variety of reasons, primarily because of the associated reduction in reaction volumes and increases in process throughput. From a process scaling standpoint, it is advantageous to refold under conditions that do not require aerobic conditions; such conditions can be achieved, for example, by constant or intermittent sparging, the implementation of air or oxygen headspace overlays, by pressurizing the headspace, or by employing high efficiency mixing. Since the oxygen concentration in the system is related to mass transfer, the scaling of the refold reaction becomes considerably more difficult as factors such as tank geometry, volume, and mixing change. Furthermore, oxygen may not be a direct reactant in the formation of disulfide bonds in the protein, making a direct link to the mass transfer coefficient unlikely. This further complicates scaling of the reaction. Therefore, non-aerobic, chemically controlled redox systems are preferred for refolding proteins. Examples of such conditions are provided herein.

The optimal refold chemistry for a given protein represents a careful balance that maximizes the folded/oxidized state while minimizing undesirable product species, such as aggregates, unformed disulfide bridges (e.g., reduced cysteine pairs), incorrect disulfide pairings (which can lead to misfolds), oxidized amino acid residues, deamidated amino acid residues, incorrect secondary structure, and product-related adducts (e.g., cysteine or cysteamine adducts). One factor that is important in achieving this balance is the redox-state of the refold system. The redox-state is affected by many factors, including, but not limited to, the number of cysteine residues contained in the protein, the ratio and concentration of the redox couple chemicals in the refold solution (e.g., cysteine, cystine, cystamine, cysteamine, glutathione-reduced and glutathione-oxidized), the concentration of reductant carried over from the solubilization buffer (e.g., DTT, glutathione and beta-mercaptoethanol), the level of heavy metals in the mixture, and the concentration of oxygen in the solution.

Thiol-pair ratio and thiol-pair buffer strength are defined in Equations 1 and 2, infra, using cysteine and cystamine as an example reductant and oxidant, respectively. These quantities, coupled with protein concentration and reductant carryover from the solubilization, can be factors in achieving a balance between the thiol-pair ratio and the thiol-pair buffer strength.

Turning to FIG. 1, this figure depicts the effect of thiol-pair ratio and thiol buffer strength on the distribution of product-related species, as visualized by reversed phase-HPLC analysis, for a complex dimeric protein. In FIGS. 1*a*-1*f*, the dotted lines represent protein species with oxidized amino acid residues, single chain species, and stable mixed disulfide intermediates, the dashed lines represent mis-paired or incorrectly formed disulfide protein species and protein species with partially unformed disulfide linkages. The solid lines represent properly folded protein species. FIGS. 1*a*-1*f* demonstrate that at a constant 6 g/L protein concentration, as the thiol-pair buffer strength is increased, the thiol-pair ratio required to achieve a comparable species distribution must also increase. For example, as shown in FIG. 1, if the buffer strength is increased to 10 mM, from 5 mM, the balanced thiol-pair ratio would be about 2-fold higher, to achieve a comparable species distribution. This is largely due to increased buffering of the reductant carried over from the solubilization, on the total system thiol-pair ratio. At lower redox buffer strengths, the overall system becomes much more difficult to control. The protein concentration and number of cysteines contained in the protein sequence also relate to the minimum required thiol-pair buffer strength required to control the system. Below a certain point, which will vary from protein to protein, the protein thiol concentration can overwhelm the redox couple chemistry and lead to irreproducible results.

In the results depicted in FIG. 1, when the thiol-pair ratio of the refolding solution is intentionally set to be more reducing, the resultant product distribution shifts to produce more of the reduced product species (dashed lines). When the Thiol-Pair Ratio of the refolding solution is intentionally set to be lower, or more oxidizing, the resultant product distribution shifts to produce more oxidized residues, single chain forms, and stable mixed disulfide intermediate species (dotted lines). The ability to select an optimal Thiol-Pair Ratio and Thiol-pair Buffer Strength allows for the optimization of the yield of a desired folded protein form. This optimized yield can be achieved by maximizing the mass or yield of desired folded protein species in the refolding pool or by purposefully shifting the resultant undesired product-related species to a form that is most readily removed in the subsequent purification steps and thusly leads to an overall benefit to process yield or purity.

Optimization of the redox component Thiol-pair Ratios and Thiol-pair Buffer Strengths can be performed for each protein. A matrix or series of multifactorial matrices can be evaluated to optimize the refolding reaction for conditions that optimize yield and distributions of desired species. An optimization screen can be set up to systematically evaluate redox chemistries, Thiol-pair ratios, Thiol-pair Buffer Strengths, incubation times, protein concentration and pH in a full or partial factorial matrix, with each component varied over a range of at least three concentration or pH levels with all other parameters kept constant. The completed reactions can be evaluated by RP-HPLC and SE-HPLC analysis for yield and product quality using standard multivariate statistical tools.

III. Method Of Refolding A Protein Expressed In A Non-Mammalian Expression System And Present In A Volume At A Concentration Of 2.0 G/L Or Greater The disclosed refold method is particularly useful for refolding proteins expressed in non-mammalian expression systems. As noted herein, non-mammalian cells can be engineered to produce recombinant proteins that are expressed intracellularly in either a soluble or a completely insoluble or non-native limited solubility form. Often the cells will deposit the recombinant proteins into large insoluble or limited solubility aggregates called inclusion bodies. However, certain cell growth conditions (e.g., temperature or pH) can be modified to drive the cells to produce a recombinant protein in the form of intracellular, soluble monomers. As an alternative to producing proteins in insoluble inclusion bodies, proteins can be expressed as soluble proteins, including proteins comprising an Fc region, which can be captured directly from cell lysate by affinity chromatography. Capturing directly from lysate allows for the refolding of relatively pure protein and avoids the very intensive harvesting and separation process that is required in inclusion body processes. The refolding method, however, is not limited to samples that have been affinity purified and can be applied to any sample comprising a protein that was expressed in a non-mammalian expression system, such as a protein found in a volume of cell lysate (i.e., a protein that has not been purified in any way).

In one aspect, the present disclosure relates to a method of refolding a protein expressed in a non-mammalian expression system in a soluble form and present in a volume at a concentration of 2.0 g/L or greater, such as a protein that has been purified by affinity chromatography from the cell lysate of non-mammalian cells in which the protein was expressed. Although the volume can be derived from any stage of a protein purification process, in one example the volume is an affinity chromatography elution pool (e.g., a Protein A elution pool). In another example, the volume is situated in a process stream. The method is not confined to Fc-containing proteins, however, and can be applied to any kind of peptide or protein that is expressed in a soluble form and captured from non-mammalian-derived cell lysate. The isolated soluble protein is often released from non-mammalian cells in a reduced form and therefore can be prepared for refolding by addition of a denaturant, such as a chaotrope. Further combination with protein stabilizers, aggregation suppressors and redox components, at an optimized Thiol-pair ration and Thiol-pair Buffer Strength, allows for refolding at concentrations of 1-40 g/L, for example at concentrations of 10-20 g/L.

In one particular embodiment of the method, a protein is expressed in a non-mammalian expression system, and is released from the expressing cell by high pressure lysis. The protein is then captured from the lysate by Protein A affinity chromatography and is present in a volume at a concentration of 10 g/L or greater. The protein is then contacted with a refold buffer comprising a denaturant, an aggregation suppressor, a protein stabilizer and a redox component, wherein the redox component has a final thiol-pair ratio (as defined herein) having a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50 and a Thiol-pair buffer strength (as defined herein) equal to or greater than 2 mM, for example greater than or equal to 2.25 mM, 2.5, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM.

In another aspect, the present disclosure relates to a method of refolding a protein expressed in a non-mammalian expression system in an insoluble or limited-solubility form, such as in the form of inclusion bodies. When the protein is disposed in inclusion bodies, the inclusion bodies can be harvested from lysed cells, washed, concentrated and refolded.

Optimization of the refold buffer can be performed for each protein and each final protein concentration level using the novel method provided herein. As shown in the Examples, good results can be obtained when refolding a protein comprising an Fc region when the refold buffer contains a denaturant (e.g., urea or other chaotrope, organic solvent or strong detergent), aggregation suppressors (e.g., a mild detergent, arginine or low concentrations of PEG), protein stabilizers (e.g., glycerol, sucrose or other osmolyte, salts) and redox components (e.g., cysteine, cystamine, glutathione). The optimal thiol-pair ratio and redox buffer strength can be determined using an experimental matrix of thiol-pair ratio (which can have a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50) versus thiol-pair buffer strength (which can be greater than 2 mM, for example greater than or equal to 2.25 mM, 2.5, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM, depending on the protein concentration and the concentration of reductant used to solubilize the inclusion bodies). Conditions can be optimized using the novel methods described in Example 2.

In one particular embodiment of the method, a protein is expressed in a non-mammalian expression system and is present in a volume at a concentration of 2.0 g/L or greater. The protein is contacted with a refold buffer comprising a denaturant, an aggregation suppressor, a protein stabilizer and a redox component, wherein the redox component has a final thiol-pair ratio (as defined herein) having a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50, and a Thiol-pair buffer strength (as defined herein) equal to or greater than 2 mM, for example greater than or equal to 2.25 mM, 2.5 mM, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM.to form a mixture. A wide range of denaturant types may be employed in the refold buffer. Examples of some common denaturants that can be employed in the refold buffer include urea, guanidinium, dimethyl urea, methylurea, or ethylurea. The specific concentration of the denaturant can be determined by routine optimization, as described herein.

A wide range of protein stabilizers or aggregation suppressors can be employed in the refold buffer. Examples of some common aggregation suppressors that can be useful in the refold buffer include arginine, proline, polyethylene glycols, non-ionic surfactants, ionic surfactants, polyhydric alcohols, glycerol, sucrose, sorbitol, glucose, Tris, sodium sulfate, potassium sulfate, other osmolytes, or similar compounds. The specific concentration of the aggregation suppressor can be determined by routine optimization, as described herein.

A redox component of the refold buffer can be of any composition, with the caveat that the redox component has a final thiol-pair ratio in a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50, and a Thiol-pair buffer strength of greater than or equal to 2 mM, for example greater than or equal to 2.25 mM, 2.5, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM. Methods of identifying a suitable redox component, i.e., determining appropriate thiol-pair ratios and redox buffer strengths, are known and/or are provided herein. Examples of specific thiol pairs that can form the redox component can include one or more of reduced glutathione, oxidized glutathione, cysteine, cystine, cysteamine, cystamine, and beta-mercaptoethanol. Thus, a thiol-pair can comprise, for example, reduced glutathione and oxidized glutathione. Another example of a thiol pair is cysteine and cystamine. The redox component can be optimized as described herein.

After the protein has been contacted with a redox component having the recited thiol pair ratio and redox buffer strength to form a refold mixture, the refold mixture is then incubated for a desired period of time. The incubation can be performed under non-aerobic conditions, as defined herein. Non-aerobic conditions need not be completely free of oxygen, only that no additional oxygen other than that present in the initial system is purposefully introduced. The incubation period is variable and is selected such that a stable refold mixture can be achieved with the desired analytical properties. An incubation period can be, for example, 1 hour, 4 hours, 12 hours, 24 hours, 48 hours, 72 hours, or longer.

Due to the sensitivity of high concentration refolds to the level of oxygen present in the system and the tendency for oxygen mass transfer to be greater at small-scale, a methodology and/or apparatus can be developed to control the oxygen levels and maintain non-aerobic conditions for the incubation step. In one embodiment, the procedure can comprise the preparation, dispensing and mixing of all refold components under a blanket of inert gas, such as nitrogen or argon, to avoid entraining levels of oxygen into the reaction. This approach is particularly helpful in identifying an acceptable thiol-pair ratio. In another embodiment useful at scales of 15 liters or less, the headspace of the refold reactor containing the protein and refold buffer can be purged with an inert gas or a mixture of inert gas and air or oxygen, and the reaction vessel sealed and mixed at a low rotational speed for the duration of the incubation time.

Following the incubation, the protein is isolated from the refold mixture. The isolation can be achieved using any known protein purification method. If the protein comprises a Fc domain, for example, a Protein A column provides an appropriate method of separation of the protein from the refold excipients. In other embodiments, various column chromatography strategies can be employed and will depend on the nature of the protein being isolated. Examples include HIC, AEX, CEX and SEC chromatography. Non-chromatographic separations can also be considered, such as precipitation with a salt, acid or with a polymer such as PEG (see, e.g., US 20080214795). Another alternative method for isolating the protein from the refold components can include dialysis or diafiltration with a tangential-flow filtration system.

In another exemplary refolding operation, inclusion bodies obtained from a non-mammalian expression system are solubilized in the range of 10 to 100 grams of protein per liter and more typically from 20-40 g/L for approximately 10-300 min. The solubilized inclusion bodies are then diluted to achieve reduction of the denaturants and reductants in the solution to a level that allows the protein to refold. The dilution results in protein concentration in the range of 1 to 15 g/L in a refold buffer containing urea, glycerol or sucrose, arginine, and the redox pair (e.g., cysteine and cystamine). In one embodiment the final composition is 1-4 M urea, 5-40% glycerol or sucrose, 25-500 mM arginine, 0.1-10 mM cysteine and 0.1-10 mM cystamine. The solution is then mixed during incubation over a time that can span from 1 hour to 4 days.

As noted herein, the disclosed method is particularly useful for proteins expressed in bacterial expression systems, and more particularly in bacterial systems in which the protein is expressed in the form of inclusion bodies within the bacterial cell. The protein can be a complex protein, i.e., a protein that (a) is larger than 20,000 MW, or comprises greater than 250 amino acid residues, and (b) comprises two or more disulfide bonds in its native form. When the protein is expressed in an inclusion body it is likely that any disulfide bond found in the protein's native form will be misformed or not formed at all. The disclosed method is applicable to these and other forms of a protein of interest. Specific examples of proteins that can be considered for refolding using the disclosed methods include antibodies, which are traditionally very difficult to refold at high concentrations using typical refold methods due to their relatively large size and number of disulfide bonds. The method can also be employed to refold other Fc-containing molecules such as peptibodies, and more generally to refold any fusion protein comprising an Fc domain fused to another protein.

Another aspect of the disclosed method is its scalability, which allows the method to be practiced on any scale, from bench scale to industrial or commercial scale. Indeed, the disclosed method will find particular application at the commercial scale, where it can be employed to efficiently refold large quantities of protein.

The present disclosure will now be illustrated by reference to the following examples, which set forth certain embodiments. However, it should be noted that these embodiments are illustrative and are not to be construed as restricting the invention in any way.

EXAMPLES

The Examples presented herein demonstrate that thiol-pair ratio and redox buffer strength is a significant consideration in achieving an efficient refolding reaction that is insensitive to environmental influences and aeration. This insensitivity is a consideration for the ease of scaling and on an industrial or commercial scale, the transfer of the process from plant to plant.

The Examples also demonstrate that at typical refolding reaction concentrations (0.01-2.0 g/L); the sensitivity to external aeration is relatively muted. However, at concentrations of about 2 g/L and above, the sensitivity of the refold reaction to the thiol-pair ratio and redox buffer strength is increased and nearly all of the chemical components, especially the redox components, may need to be adjusted to accommodate for changes in the protein concentration in the reaction.

Example 1

Expression of Recombinant Protein

In one experiment, recombinant proteins comprising an Fc moiety were expressed in a non-mammalian expression system, namely *E coli*, and driven to form cytoplasmic deposits in the form of inclusion bodies. For each protein refolded the following procedure was followed.

After the completion of the expression phase, the cell broth was centrifuged and the liquid fraction removed, leaving the cells as a paste. The cells were resuspended in water to approximately 60% of the original volume. The cells were then lysed by means of three passes through a high pressure homogenizer. After the cells were lysed, the lysate was centrifuged in a disc-stack centrifuge to collect the protein in the solid fraction, which was expressed in a limited solubility non-native form, namely as inclusion bodies. The protein slurry was washed multiple times by repeatedly resuspending the captured solids slurry in water to between 50% and 80% of the original fermentation broth volume, mixing, and centrifugation to collect the protein in the solid fraction. The final washed inclusion bodies were captured and stored frozen.

Example 2

Identification of Refold Conditions/Redox Components

Multiple complex, microbial-derived proteins were evaluated. Each protein was solubilized in an appropriate level of guanidine and/or urea, typically at levels the equivalent of 4-6 M guanidine or 4-9 M urea, or combinations of both denaturants, which fully denatured the protein. The protein was reduced with DTT, 5-20 mM, at pH 8.5, and incubated at room temperature for approximately 1 hour.

Identification of the refold buffer was performed for each protein. A multifactorial matrix or a series of multifactorial matrices were evaluated to identify the refolding reaction for conditions that optimize yield and minimize aggregate formation. An identification screen was set up to systematically evaluate urea, arginine, glycerol and pH in a full factorial matrix, with each component varied over a range of at least three concentration or pH levels with all other parameters kept constant. The completed reactions were evaluated by RP-HPLC and SE-HPLC analysis for yield and product quality using standard multivariate statistical tools. A subset of the conditions having the desired behavior was then further evaluated in subsequent screens that evaluated a range of pH, thiol-pair ratio, thiol-pair buffer strength, and potentially further excipient levels in a factorial screen. Secondary interactions were also evaluated using standard multivariate statistical tools.

Best results, as determined by reversed-phase and size exclusion HPLC analysis, were observed using a refold buffer containing a denaturant (e.g., urea, dimethyl urea or other chaotrope at non-denaturing levels at levels between 1 and 4 M), an aggregation suppressor (e.g., arginine at levels between 5 and 500 mM), a protein stabilizer (e.g., glycerol or sucrose at levels between 5 and 40% w/v) and a redox component (e.g., cysteine or cystamine). The thiol-pair ratio and redox buffer strength were determined using an experimental matrix of thiol-pair ratio (0.1 to 100, more typically 1 to 25) versus buffer strength (typically 2 mM to 20 mM, depending on the protein concentration, the number of cysteine residues in the protein, and the concentration of reductant used to solubilize the inclusion bodies).

Individual reactions were formed with varying levels of cysteine and cystamine that would allow for a controlled matrix of thiol-pair ratio at various thiol-pair buffer strengths. The relationships were calculated using Equations 3 and 4. Each condition was screened under both aerobic and non-aerobic conditions, utilizing the techniques described herein. Optimum conditions were selected to meet a stable balance of yield, desired distribution of folding species, insensitivity to environmental oxidants (e.g., air), and insensitivity to normal variation in DTT carry-over from the solubilization step.

Example 3

High Concentration Refolding of Non-Native Soluble Protein Form Captured from Cell Lysate In one experiment, a recombinant protein comprising a plurality of polypeptides joined to an Fc moiety was expressed in *E. coli* as an intracellular soluble peptide chain, lysed from harvested and washed cells, isolated from the lysate by affinity chromatography, and then refolded at a concentration of approximately 12 g/L, as described herein.

After the completion of the expression phase, an aliquot of whole fermentation broth was centrifuged and the liquid fraction removed, leaving the cells as a paste. The cells were resuspended in water to approximately 60% of the original volume. The cells were then lysed by means of three passes through a high pressure homogenizer. After the cells were lysed, the lysate pool was mixed in the presence of air for 8-72 hours to allow for dimerization of the peptide chains. Following the dimerization process, the peptide chain of interest was isolated from the lysate pool using a Protein A affinity chromatography column. The Protein A column elution pool was mixed at a ratio of 8 parts Protein A elution material to 2 parts of a refold buffer containing urea (10 M), arginine-HCl (2.5 M), Tris at pH 8.5 (1050 mM), and cysteine (10 mM, 5 mM, or 4 mM) and cystamine (4 mM). The diluted mixture was titrated to pH 8.5 and incubated at approximately 5° C. under nitrogen until a stable pool was achieved (~24 hours.) Yields of desired product of approximately 30-80% were obtained a depending on the redox condition evaluated.

In order to emulate the non-anaerobic conditions similar to those typically present in very large-scale protein production processes several steps were taken. When reaction volumes were less than approximately 15 L the refold vessel headspace was purged with nitrogen to limit the effect oxygen could have in the system. The vessel was then sealed and incubation began.

When reaction volumes were more than approximately 15 L but less than 500 L, the refold buffer was prepared and allowed to equilibrate at approximately 5° C. to achieve a stable oxygen level in the solution (typically 50% to 70% dissolved oxygen, relative to air saturation). Once the refold mixture was formed, the vessel headspace was purged with nitrogen to limit any additional effect oxygen could have in the system, the vessel was sealed and incubation period initiated.

Example 4

High Concentration Refolding from Inclusion Bodies

In one experiment, a recombinant protein comprising a biologically active peptide linked to the C-terminus of the Fc moiety of an IgG1 molecule via a linker and having a molecular weight of about 57 kDa and comprising 8 disulfide bonds, was expressed in *E. coli* as inclusion bodies, harvested, washed, concentrated, solubilized, and refolded at a concentration of 6 g/L as described herein.

An aliquot of frozen concentrated inclusion bodies were thawed to room temperature and mixed with an appropriate amount of guanidine and/or urea to generate a denaturant level equivalent to 4-6 M guanidine, which fully denatures the protein. The protein was then reduced with DTT, at 5-20 mM, at pH 8.5, and incubated at room temperature for approximately 1 hour. After the inclusion bodies were dissolved, denatured and reduced, they were diluted into a refold buffer containing urea (1-5 M), arginine-HCl (5-500 mM), glycerol (10-30% w/v), and the identified levels of cysteine and cystamine as determined by the procedure described in Example 2. The final component concentrations are 4 M urea, 150 mM arginine HCl, 20.9% (w/v) glycerol, 2.03 mM cysteine, and 2.75 mM cystamine. The level of dilution was chosen to balance the dilution of the denaturants from the solubilization, maintain the thermodynamic stability of the molecule during refolding, and maintain the highest possible protein concentration in the refold mixture. The diluted mixture was titrated to an alkaline pH (between pH 8 and pH 10) and incubated at 5° C. under non-aerobic conditions until a stable pool was achieved (12-72 hours), as determined by relevant analytical measurements. The resulting process was demonstrated to show stable scalablity from 1 L-scale to 2000 L-scale (see FIG. 3). Yields of desired product of approximately 27-35% were obtained at both scales. The distribution of product related impurities was also maintained within a tight variance (see FIG. 3).

Oxygen mass transfer at small-scale is readily achieved and should be inhibited in order to emulate the relatively poorer mass transfer observed at large-scale, where the volume of refold solution is large relative to the volume of air and surface area present at the surface of a large-scale vessel. Thus, in order to emulate the non-anaerobic conditions similar to those typically present in very large-scale protein production processes several steps were taken. When reaction volumes were less than approximately 15 L the refold buffer was sparged with nitrogen to strip oxygen from the solution, the components were dispensed under a blanket of nitrogen and once the refold mixture was formed, the vessel headspace was purged with nitrogen to limit the effect oxygen could have in the system. The vessel was then sealed and incubation began.

When reaction volumes were more than approximately 15 L but less than 500L, the refold buffer was prepared and allowed to equilibrate at approximately 5° C. to achieve a stable oxygen level in the solution (typically 50% to 70% dissolved oxygen, relative to air saturation). Once the refold mixture was formed, the vessel headspace was purged with nitrogen to limit any addition effect oxygen could have in the system, the vessel was sealed and the incubation period was initiated.

At scales greater than 500 L the refold buffer was prepared and allowed to equilibrate at approximately 5° C. to achieve a stable oxygen level in the solution (typically 50% to 70% dissolved oxygen, relative to air saturation). Once the refold mixture was formed, the vessel was sealed and the incubation period was initiated.

The protein concentration of the refold mixture was 6 g/L, which is a four-fold enhancement over the recovery of 1.5 g/L obtained using a method other than the method described in this Example. Overall annual process productivity, in one specific manufacturing facility, was calculated to be increased by >930% due to increased volumetric efficiency in the existing facility tanks.

Example 5

Effect of Thiol-Pair Oxidation State on Disulfide Pairings

FIGS. 1a-1f demonstrate that as the thiol-pair ratio is forced to a more oxidizing state (lower thiol-pair ratio), a higher proportion of product species have oxidized amino acid residues and mixed disulfide forms. As the thiol-pair ratio is driven to a more reductive state (higher thiol-pair ratio), this results in lower levels of oxidized amino acid variant species and higher levels of product species with incorrect disulfide pairings or unformed disulfide bonds. As the overall thiol-pair buffer strength is modified, the corresponding optimal thiol-pair ratio is shifted. This effect is similar to how buffer strength modulates the sensitivity of pH to acid and base additions in a buffered solution.

An optimal balance of species was attainable. As shown in FIGS. 1a-1f, there is a clear relationship between thiol-pair buffer strength and thiol-pair ratio that can be identified to maintain the optimal species balance and thus facilitate efficient refolding of low solubility proteins. The ability to control product variant species, such as incorrectly disulfide-bonded species and misfolded species, via modulation of the thiol-pair ratio and thiol-pair buffer strength, enables efficient, effective and reliable subsequent purification processes.

Example 6

Effect of Non-Aerobic Conditions on Refolding Efficiency

Figure 2:
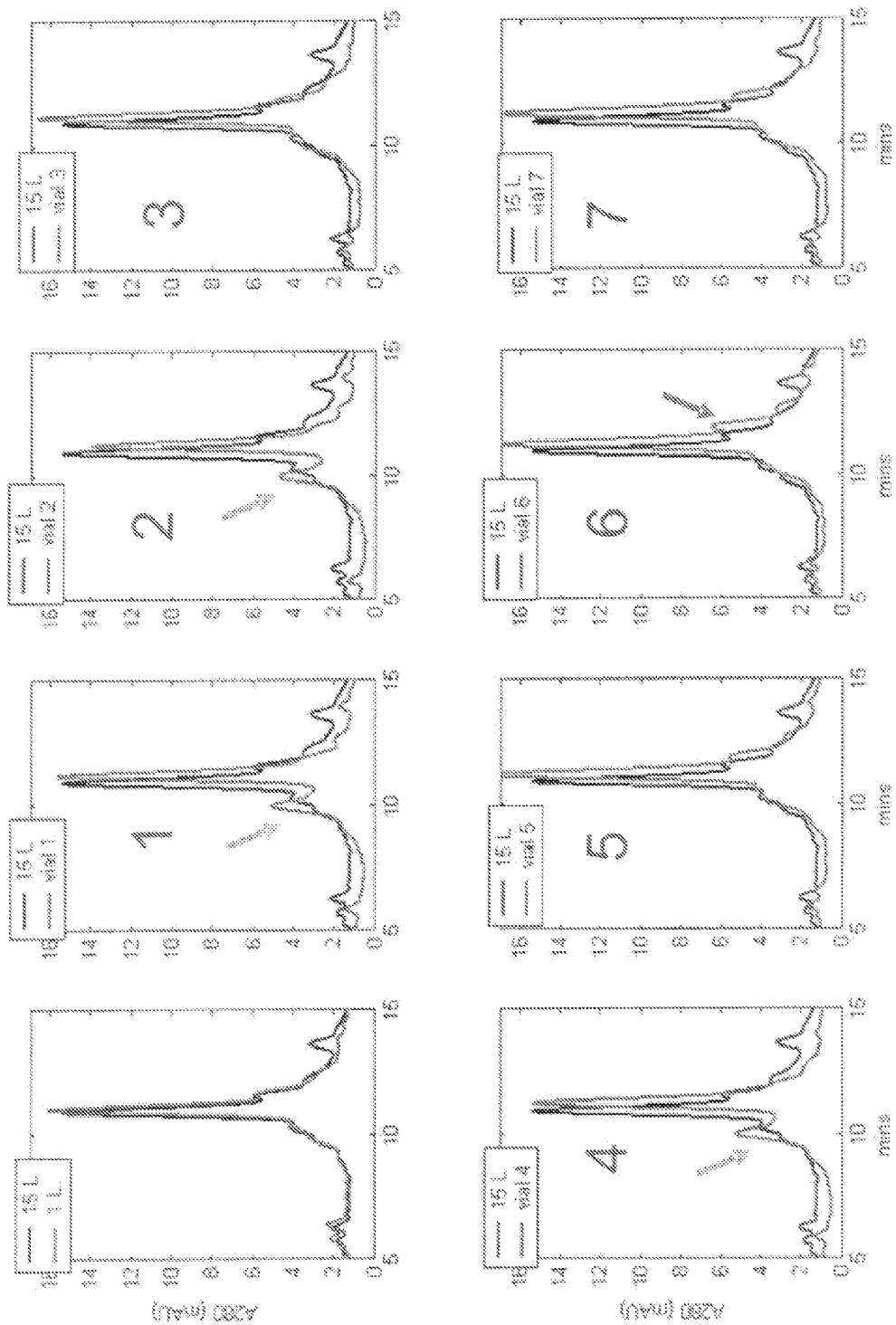
FIG. 2 is a series of plots depicting the effect of the degree of aeration on the species distribution under fixed thiol-pair ratio and thiol-pair buffer strength.
Figure 3:
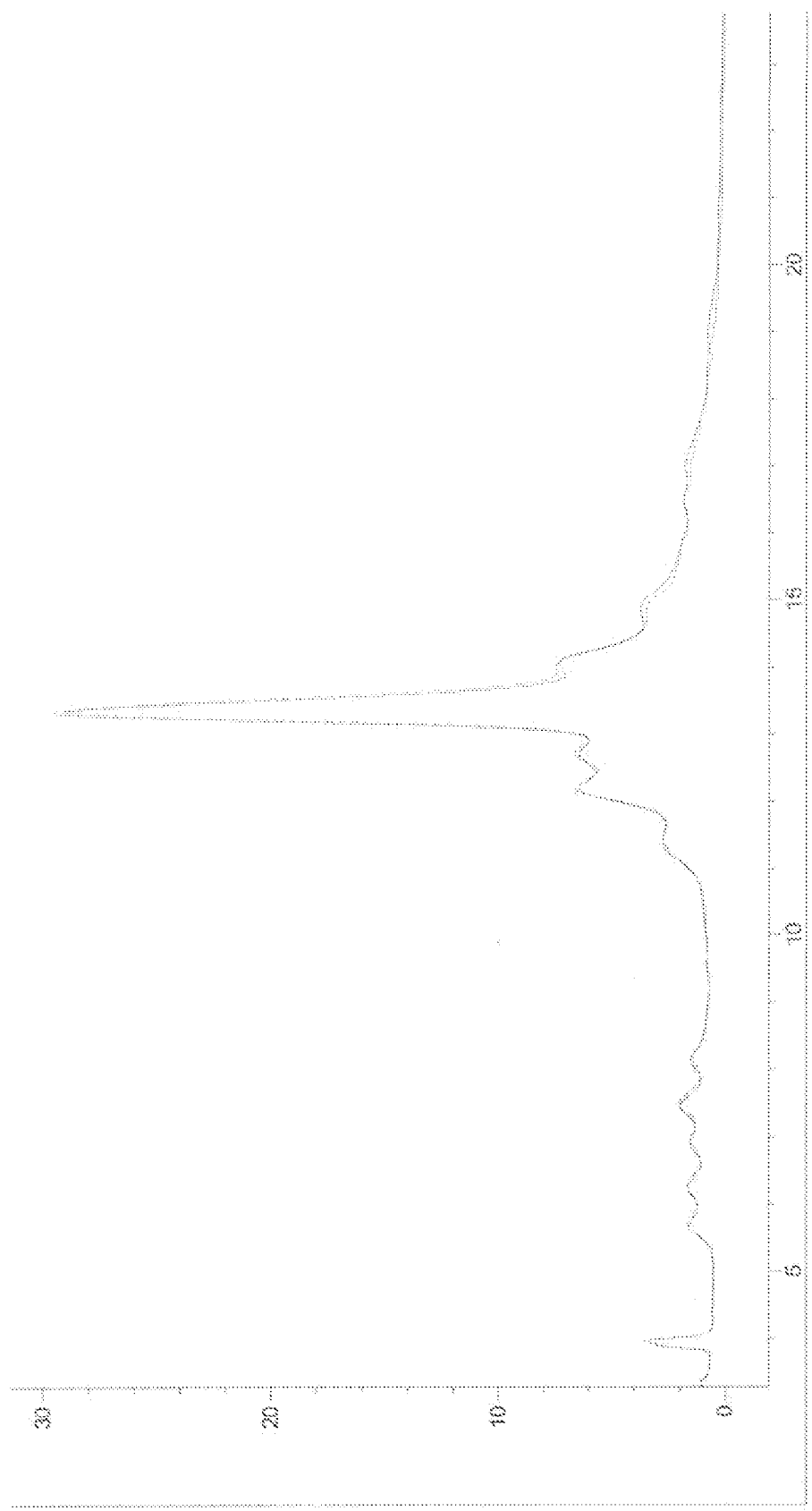
FIG. 3 is an analytical overlay of a chemically controlled, non-aerobic refold performed at 6 g/L and optimized using an embodiment of the described method performed at 1 L and 2000 L.

FIGS. 2 and 3 demonstrate that when the thiol-pair buffer strength is selected appropriately, taking into account the protein concentration and number of cysteine residues in the protein, the sensitivity to external influences, such as oxygen, is significantly reduced. This allows for a non-aerobic refolding condition that is significantly easier to transfer between scales and reactor configurations.

FIG. 2 compares the RP-HPLC analytical species distribution between a 15 L-scale refold and a 20 mL-scale refold under several environmental conditions. For Condition 1 (the trace labeled "1" in FIG. 1), the solubilization chemicals and solutions were dispensed in air and the refold mixture was incubated in air. In Condition 2 solubilization chemicals and solutions were dispensed in air and incubated under nitrogen headspace. In Conditions 3-7 solubilization chemicals and solutions were dispensed under nitrogen overlay conditions and in conditions 3, 5, 6, and 7 solubilization chemicals and solutions were incubated under nitrogen. In Condition 7, the refold solution was also stripped of nitrogen prior to combination with the solubilization solution. In Condition 4 the solubilization chemicals and solutions were incubated under ambient air conditions.

The results shown in FIG. 2 demonstrate that the conditions under which the solubilization chemicals and solutions were dispensed or incubated in the presence of air (i.e., Conditions 1, 2, and 4) do not achieve results that are comparable to the larger-scale control. In Conditions 1, 2 and 4, increased formation of oxidized species (pre-peaks) are observed. The pre-peaks are indicated by arrows in the panels for Conditions 1, 2 and 4.

FIG. 3 compares the RP-HPLC analytical results of an identified condition, achieved as described in Example 2, at 1 L-scale and 2000 L-scale. In this figure, essentially no difference in the distribution of species is detectable. Taken together, FIGS. 2 and 3 demonstrate that when aeration is carefully controlled, the small-scale refold reactions are more predictive of those expected upon scale-up of the refold reaction, facilitating the implementation of large-scale protein refolding processes.

What is claimed is:

1. A method of refolding a protein expressed in a non-mammalian expression system and present in a volume at a concentration of 2.0 g/L or greater comprising:
   (a) contacting the protein with a refold buffer comprising a redox component comprising a final thiol-pair ratio having a range of 0.001 to 100 and a redox buffer strength of 2 mM or greater and one or more of:
      (i) a denaturant;
      (ii) an aggregation suppressor; and
      (iii) a protein stabilizer;
   to form a refold mixture;
   (b) incubating the refold mixture; and
   (c) isolating the protein from the refold mixture.

2. The method of claim 1, wherein the final thiol-pair ratio is selected from the group consisting of 0.05 to 50, 0.1 to 50, 0.25 to 50, 0.5 to 50, 0.75 to 40, 1.0 to 50 and 1.5 to 50, 2 to 50, 5 to 50, 10 to 50, 15 to 50, 20 to 50, 30 to 50 or 40 to 50.

3. The method of claim 1, wherein the thiol-pair buffer strength is selected from the group consisting of greater than or equal to 2.25 mM, 2.5 mM, 2.75 mM, 3 mM, 5 mM, 7.5 mM, 10 mM and 15 mM.

4. The method of claim 1, wherein the protein is present in the volume in a non-native limited solubility form.

5. The method of claim 4, wherein the non-native limited solubility form is an inclusion body.

6. The method of claim 1, wherein the protein is present in the volume in a soluble form.

7. The method of claim 1, wherein the protein is recombinant.

8. The method of claim 1, wherein the protein is an endogenous protein.

9. The method of claim 1, wherein the protein is an antibody.

10. The method of claim 1, wherein the protein is a complex protein.

11. The method of claim 1, wherein the protein is a multimeric protein.

12. The method of claim 1, wherein the protein is an Fc-protein conjugate.

13. The method of claim 1, wherein the non-mammalian expression system is one of a bacterial expression system and a yeast expression system.

14. The method of claim 1, wherein the denaturant is selected from the group consisting of urea, guanidinium salts, dimethyl urea, methylurea and ethylurea.

15. The method of claim 1, wherein the protein stabilizer is selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes.

16. The method of claim 1, wherein the aggregation suppressor is selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes.

17. The method of claim 1, wherein the thiol-pairs comprise at least one component selected from the group consisting of glutathione-reduced, glutathione-oxidized, cysteine, cystine, cysteamine, cystamine and beta-mercaptoethanol.

18. The method of claim 1, wherein the incubation is performed under non-aerobic conditions.

19. The method of claim 1, wherein the isolation comprises contacting the mixture with an affinity separation matrix.

20. The method of claim 19, wherein the affinity separation matrix is a Protein A resin.

21. The method of claim 19, wherein the affinity resin is a mixed mode separation matrix.

22. The method of claim 1, wherein the isolating comprises contacting the mixture with an ion exchange separation matrix.

23. The method of claim 1, wherein the isolating further comprises a filtration step.

24. The method of claim 23, wherein the filtration step comprises depth filtration.

* * * * *